United States Patent
Nakamura

(10) Patent No.: US 7,104,680 B2
(45) Date of Patent: Sep. 12, 2006

(54) THERMAL ANALYZER WITH GAS MIXING CHAMBER

(75) Inventor: Toshihiko Nakamura, Chiba (JP)

(73) Assignee: SII NanoTechnology Inc., (JP)

( * ) Notice: Subject to any disclaimer, the term of this patent is extended or adjusted under 35 U.S.C. 154(b) by 57 days.

(21) Appl. No.: 10/974,853

(22) Filed: Oct. 27, 2004

(65) Prior Publication Data

US 2005/0123020 A1    Jun. 9, 2005

(30) Foreign Application Priority Data

Oct. 31, 2003 (JP) ............................. 2003-372868
Oct. 26, 2004 (JP) ............................. 2004-312149

(51) Int. Cl.
  *G01N 25/16*    (2006.01)
(52) U.S. Cl. ............................. 374/55; 374/56; 374/45
(58) Field of Classification Search ................. 374/55, 374/56, 34, 33, 38, 42
   See application file for complete search history.

(56) References Cited

U.S. PATENT DOCUMENTS

| 3,589,167 | A | * | 6/1971 | Hill | ............................. 374/56 |
| 4,976,549 | A | * | 12/1990 | Khan | ............................. 374/56 |
| 5,099,096 | A | * | 3/1992 | Kimrey et al. | ............................. 219/705 |
| 5,826,983 | A | * | 10/1998 | Nakamura et al. | ............................. 374/14 |
| 6,672,759 | B1 | * | 1/2004 | Feger | ............................. 374/56 |

FOREIGN PATENT DOCUMENTS

| DE | 3714988 | A1 | * | 11/1988 |
| GB | 2068123 | A | * | 8/1981 |
| JP | 59171843 | A | * | 9/1984 |

* cited by examiner

Primary Examiner—Diego Gutierrez
Assistant Examiner—Mirellys Jagan
(74) Attorney, Agent, or Firm—Adams & Wilks

(57) ABSTRACT

In a thermomechanical measuring device and a thermogravimetry device, partition walls are provided in two sections such that two kinds of atmospheric gasses, which have passed a sample chamber and a detector chamber, respectively, do not flow back, and a thermally insulated gas mixing chamber is manufactured anew in the middle of the sample chamber and the detector chamber to make it possible to dilute a reactive gas and a water vapor gas having a high partial pressure. Consequently, it is possible to prevent moisture concentration to reduce an influence of water drops even in a high temperature and high humidity state at the time of humidity control and measurement.

6 Claims, 5 Drawing Sheets

THERMAL ANALYZER WITH GAS MIXING CHAMBER

BACKGROUND OF THE INVENTION

The present invention relates to a thermal analyzer including a sample chamber and a detector chamber that houses a detector for detecting a physical change due to temperature of a sample stored in the sample chamber as a displacement.

In the thermal analyzer including the sample chamber and the detector chamber that houses the detector for detecting a physical change due to temperature of a sample stored in the sample chamber as a displacement, when a gas is fed, different kinds of gasses are used as an atmospheric gas in the sample chamber and am atmospheric gas in the detector chamber that is provided to be connected to the sample chamber via a tubular member. In particular, when an atmospheric gas around a sample contains water vapor, a purge gas for protecting this water moisture from condensing on the detector is introduced into the detector.

In such a case, in the conventional thermal analyzer, an exhaust port is provided in the middle between the sample chamber and the detector chamber such that the atmospheric gases and the purge gas join to be discharged out of the thermal analyzer (see, for example, Japanese Patent No. 3084472, FIG. 2 and JP-A-2002-148230, FIG. 1).

In the conventional thermal analyzer, although the two kinds of atmospheric gasses having passed the sample chamber and the detector chamber, respectively, join to be discharged, since the sample chamber and the detector chamber communicate with each other, there is a problem in that it is likely that a part of the gasses flow back to the sample chamber and the detector chamber to damage gas purge performance. As the atmospheric gas fed to the sample chamber, an inert gas or an atmospheric gas, which has interaction with a sample and affects a change in a physical amount of the sample, is often selected. A highly reactive gas or water vapor may be often contained in the atmospheric gas. In addition, a cracker gas generated from the sample may be contained in the atmospheric gas. Thus, in general, it is desirable that the thermal analyzer has a structure in which the atmospheric gas does not flow back to the detector chamber.

In the case in which the air having an adjusted water vapor pressure is fed into the sample chamber to measure a change in physical properties of the sample in an atmosphere subjected to humidity control, when the sample chamber comes into a high-temperature and high-humidity state with temperature of 80° C. and relative humidity of 60% to temperature of 90° C. and relative humidity of 90%, in the structure of the thermal analyzer for performing thermomechanical measurement (TMA) shown in FIG. 2 of Japanese Patent No. 3084472, water vapor of a high partial pressure flows to a position near an entrance on the detector side crossing the middle between sample chamber and the detector chamber. Consequently, it is likely that the water vapor is liquefied and water drops are generated on a wall surface in the middle or a surface of a sample tube or a bar probe that is closer to the detector chamber and has temperature close to a room temperature. There are problems in that, for example, a weight of the water drops adhering to the bar probe causes an error in measurement of a weight of the sample, a load applied to the sample changes to cause an error in measurement of a physical amount of the sample, and, since the thermal analyzer is constituted vertically in FIG. 2 of Japanese Patent No. 3084472, the water drops drop to a sample part below the thermal analyzer to make the relative humidity unstable.

It is an object of the invention to solve the problems and provide a thermal analyzer that prevents back-flow of atmospheric gases to a sample chamber or a detector chamber by clearly distinguishing a location where the atmospheric gasses are mixed in a process in which the atmospheric gasses join to be discharged, prevents generation of water drops by clarifying a mixing location such that a part of water vapor does not flow into the detector chamber side even in the case in which the inside of the sample chamber is subjected to humidity control to be brought into a high-temperature and high-humidity state, and makes it possible to also mix the water vapor and a dry gas on the detector chamber side to lower a concentration of a highly reactive gas or lower a partial pressure of the water vapor to make it less likely that water drops are generated.

SUMMARY OF THE INVENTION

In order to solve the problems, in a thermal analyzer of the invention, partition walls are provided in two sections on a sample chamber side and a detector side such that two kinds of atmospheric gasses having passed a sample chamber and a detector chamber, which communicates with the sample chamber, respectively, do not flow back, and a gas mixing chamber serving as a partition chamber is disposed between the sample chamber and the detector chamber. A bar member extending from the sample chamber to the detector chamber through the gas mixing chamber is a balance beam in the case of a thermogravimetry device (TG) or a detection bar, which transmits a change in a sample length and a signal of a load, in the case of a thermomechanical measuring device (TMA). Therefore, the bar member cannot measure a change in a physical amount of a sample accurately when the bar member mechanically comes into contact with the partition walls. Thus, holes for gas flow larger in diameter than a diameter of the bar member are pierced near the center of the partition walls to prevent the bar member from coming into contact with the partition walls.

When it is difficult to alter the structure to provide a gas mixing chamber anew in the existing thermal analyzer, it is possible to provide partition members, which are made of a flexible material and have holes in the center thereof, and fit the partition members in the thermal analyzer to form the partition walls. A space between the partition members functions as the gas mixing chamber, whereby the same structure as described above is obtained.

In the thermal analyzer constituted as described above, since the sample chamber, the detector chamber, and the gas mixing chamber are separated from one other by the partition walls, gasses passing through the sample chamber and the detector chamber are fed independently from the sample chamber and the detector chamber, respectively. Thus, the gasses are never mixed. In the gas mixing chamber, the two kinds of gasses are mixed and diluted and then discharged to the outside. Since the bar member is inserted through gaps provided in the respective gas-flow holes of the partition walls, the bar member is not in contact with wall surfaces of the holes of the partition walls. Thus, it is possible to perform measurement of a physical amount accurately.

DETAILED DESCRIPTION OF THE PREFERRED EMBODIMENTS

Figure 1:
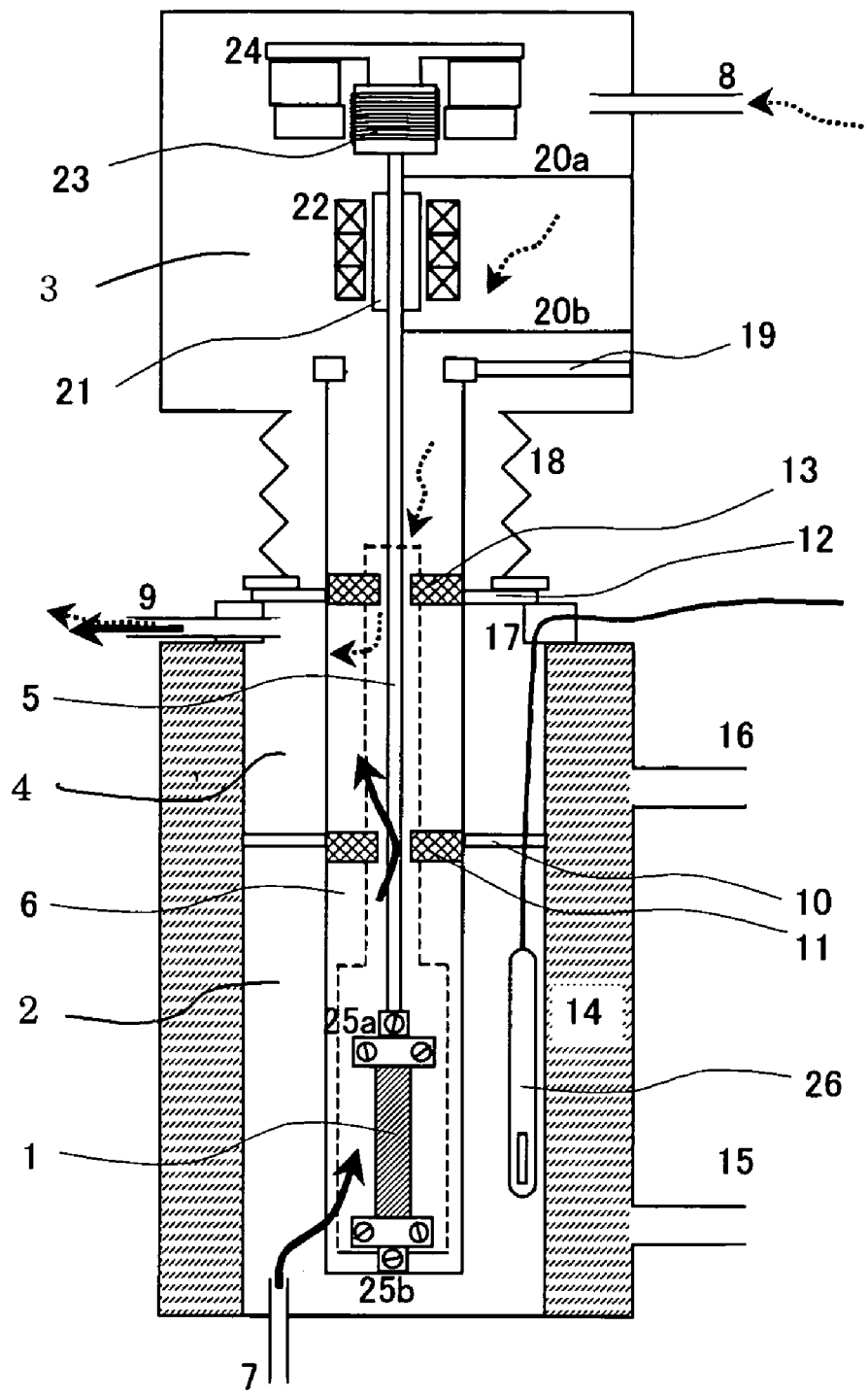
FIG. 1 is a longitudinal sectional view of a thermomechanical measuring device (TMA) to which the invention is applied.

An embodiment of the invention will be explained with reference to the accompanying drawings. FIG. 1 is a longitudinal sectional view of a thermal analyzer according to the invention. A type of the thermal analyzer is a thermomechanical measuring device (TMA). This is an example of a device that is capable of performing measurement as a humidity control type TMA assuming the air having an adjusted water vapor partial pressure as an atmospheric gas around a sample.

In FIG. 1, in an entire structure of the thermal analyzer, a sample chamber 2 is provided in a lower part, a detector chamber 3 is provided in an upper part, and a gas mixing chamber 4 is provided in the center to be placed between the sample chamber 2 and the detector chamber 3. A gas containing a water vapor gas indicated by a solid line arrow is fed to the sample chamber 2. On the other hand, a dry gas indicated by a dotted line arrow is fed to the detector chamber 3. The two kinds of gasses are mixed in the gas mixing chamber 4 and discharged to the outside. The sample chamber 2 and the gas mixing chamber 4 are provided in the inside of a hot water furnace 14, which is devised to have uniform temperature, to prevent moisture concentration.

Details of FIG. 1 will be explained. As a representative example, it is assumed that a sample 1 is a film-like sample. The sample has a size of an effective length of 20 rom, an effective width of 3 rom, and an effective thickness of about several tens μm. The sample 1 is disposed in the sample chamber 2, and the detector chamber 3, which is connected to the sample chamber 2 via a bellows 18 formed as a tubular member, is disposed above the sample chamber 2. The gas mixing chamber 4 is provided in the middle between the sample chamber 2 and the detector chamber 3. An upper end of the sample 1 is fixed to a bar member 5 made of quartz glass with a diameter of 3.5 mm by a sample chuck 25a made of metal. A lower end of the sample 1 is fixed to a cylindrical sample tube 6 made of quartz glass by a sample chuck 25b made of metal.

As indicated by a dotted line in the figure, on a side of the sample tube 6, a window for replacement of the sample 1 is opened and a vertical slit for replacement of the bar member 5 is opened extending from a sample portion to the gas mixing chamber 4. Thus, an atmospheric gas can be exchanged easily between the inside and the outside of the sample tube 6.

An atmospheric gas to be fed to the sample chamber 2 is introduced from a sample chamber gas inlet 7 provided below the sample chamber 2. An atmospheric gas to be fed to the detector chamber 3 is introduced from a detector chamber gas inlet 8 provided on a side of the detector chamber 3. A gas mixing chamber gas outlet 9 is provided in the gas mixing chamber 4. The respective atmospheric gasses are fed through a not-shown tube of resin with an outer diameter of 6 mm and an inner diameter of 4 mm. The inlets 7 and 8 and the outlet 9 for the respective gasses are made in a pipe shape and have substantially the same diameter as the tube of resin.

The sample chamber 2 and the gas mixing chamber 4 are partitioned by a disc-like ring 10 made of silicon rubber and a gap ring 11 made of foamed resin. In other words, the disc-like ring 10 and the gap ring 11 form a partition wall. Taking into account a case in which the thermal analyzer is used as a usual TNA, the partitioning portion is made of flexible resin and constituted to be easily removable. The disc-like ring 10 is fixed to an inner wall of the sample chamber 2 to cover the inner wall of the sample chamber 2 and an outer periphery of the sample tube 6 without a gap. An outer periphery of the gap ring 11 adheres to an inner periphery of the sample tube 6. However, an inner diameter of the gap ring 11 is set larger than a diameter of the bar member 5 by about 2 to 3 mm to form a gas outlet of the sample chamber 2 and provide a gap to thereby allow the bar member 5 to be inserted through the gap ring 11. The detector chamber 3 and the gas mixing chamber 4 are partitioned by a partition wall comprised of a disc-like ring 12 made of silicon rubber and a gap ring 13 made of foamed resin in the same manner. The disc-like ring 12 adheres to the outer periphery of the sample tube 6 and the gap ring 13 forms a gas outlet of the detector chamber 3 and provides a gap to allow the bar member 5 to be inserted through the gap ring 13.

It is also possible to provide the gas outlet of the sample chamber 2 and the gas outlet of the detector chamber 3 in plural places rather than one place. When it is assumed that the gas outlet, through which the bar member 5 is inserted, is a first outlet, if the first outlet having a very narrow gap between the outer periphery of the bar member 5 and the first outlet itself can be formed, the same effect is obtained when a large second outlet is provided in another place of the partition wall. The following explanation is about a case in which a sectional area obtained by cutting the second outlet with a partition wall surface around the second outlet is larger than a sectional area obtained by cutting the gap between the first outlet and the bar member 5 with a partition wall surface around the gap. Since the sectional area of the first outlet is small, an amount of a gas passing through the first outlet is small and is almost negligible in an extreme case. Thus, most of the gas passes through the second outlet with the large sectional area. When a gas flow rate is large, such a structure is effective. It is possible to form the second outlet in an appropriate size, for example, in the disc-like ring 10 or the disc-like ring 12 according to a gas flow rate.

The sample chamber 2 and the gas mixing chamber 4 form an inner space of a double cylinder type hot water furnace 14 made of stainless steel alloy. The middle of the double cylinder type hot water furnace 14 is welded and sealed. A hot water inlet 15 and a hot water outlet 16 for hot water circulation are attached to an outer wall of the double cylinder type hot water furnace 14. This makes it possible to circulate a liquid subjected to temperature adjustment in a not-shown circulation thermostatic bath or the like such that the inside of the double cylinder type hot water furnace 14 is maintained at uniform temperature. Usually, since water is circulated, a temperature range is about 2° C. to 90° C. However, when silicon oil or the like is used, it is possible to expand the temperature range. When a water vapor partial pressure is low and there is no fear of moisture concentration, an electric heater heating system using a heating wire may be adopted instead of the hot water circulation system. This system is a simple heating method, but a temperature distribution tends to occur and moisture concentration tends to occur in a part of low temperature. However, when a water vapor partial pressure is low, that is, a dew point is low, moisture concentration is less likely to occur. Thus, the electric heater heating system using the heating wire may be adopted only when the water vapor partial pressure is low.

An upper part of the double cylinder type hot water furnace 14 is opened. There is a base 17 at an upper end of the double cylinder type hot water furnace 14, and the disc-like ring 12 is placed on the base 17. When the sample 1 is attached, the double cylinder type hot water furnace 14 is lowered by a not-shown hot water furnace vertical movement mechanism to expose a lower part of the sample tube 6. At this point, since the disc-like ring 10 is fixed to an inner wall of the double cylinder type hot water furnace 14, the disc-like ring 10 falls together with the double cylinder type hot water furnace 14 while sliding on the outer periphery of the sample tube 6. When the sample 1 has been set, the double cylinder type hot water furnace 14 is lifted to return the disc-like ring 10 to an original position and the disc-like ring 12 is nipped by the base 17 to be pressed against the bellows 18. Then, sealing performance is given to the double cylinder type hot water furnace 14 by a spring restoring force of the bellows 18 to prevent the external air from entering the double cylinder type hot water furnace 14.

The detector chamber 3 is surrounded by a box of metal to prevent the external air from entering the detector chamber 3. In the inside of the detector chamber 3, there are a sample tube holding mechanism 19, cantilever leaf springs 20a and 20b made of metal for holding the bar member 5 so as to be movable up and down, a differential transformer core 21 for sample displacement detection 24 attached to the bar member 5, a differential transformer coil 22, an electromagnetic load generating coil 23 fixed to an upper end of the bar member 5, and a combination 24 of a permanent magnet and a yoke material fixed to the detector chamber 3.

A temperature and humidity sensor 26 for temperature and relative humidity detection is inserted in the sample chamber 2. A signal cable of the temperature and humidity sensor 26 is pierced through the portions of the disc-like ring 10 and the base 17 in an air tight state to be connected to the outside.

Figure 2:
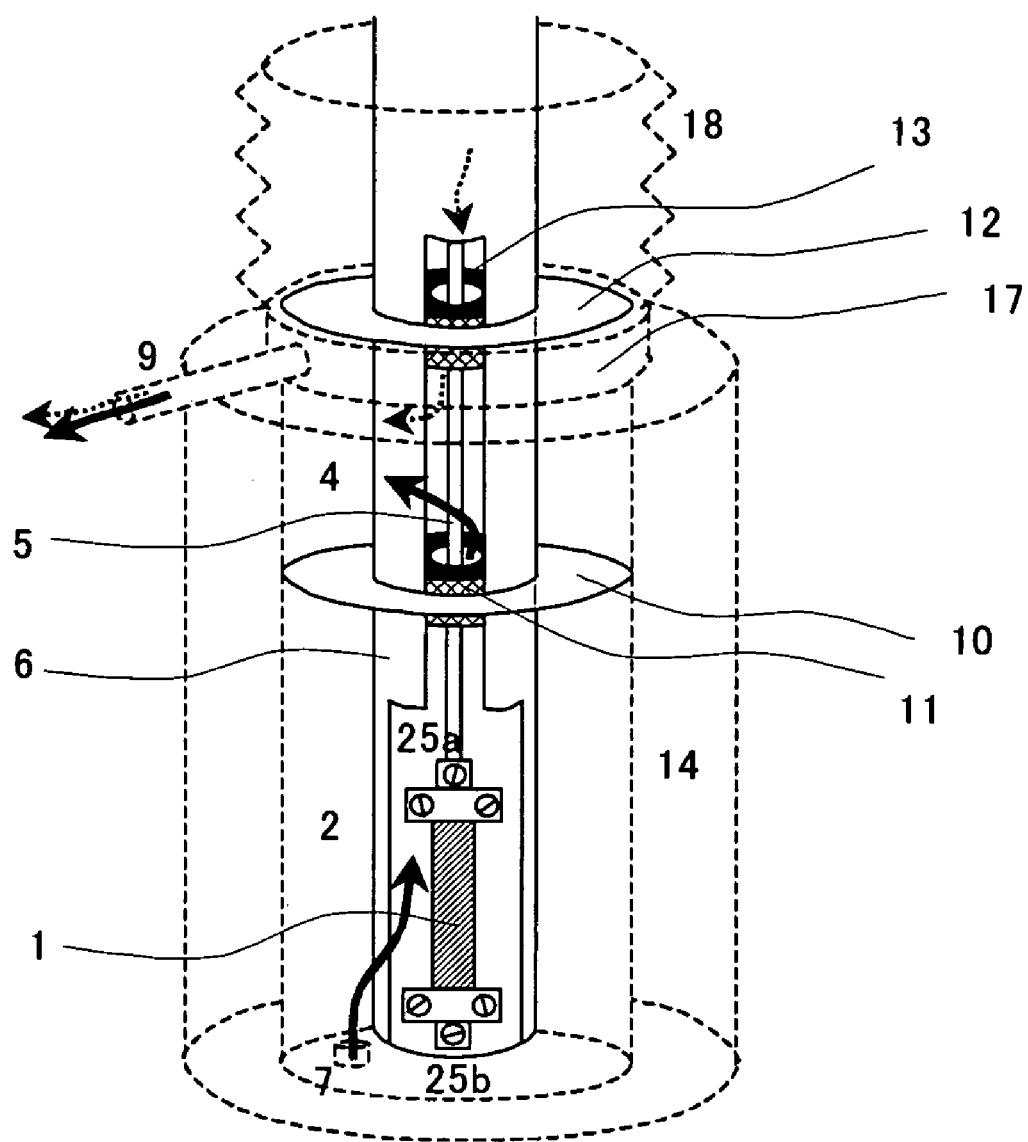
FIG. 2 is a perspective view of the thermomechanical measuring device (TMA) to which the invention is applied.

FIG. 2 is a perspective view of the thermomechanical measuring device (TMA) shown in FIG. 1.

Figure 3:
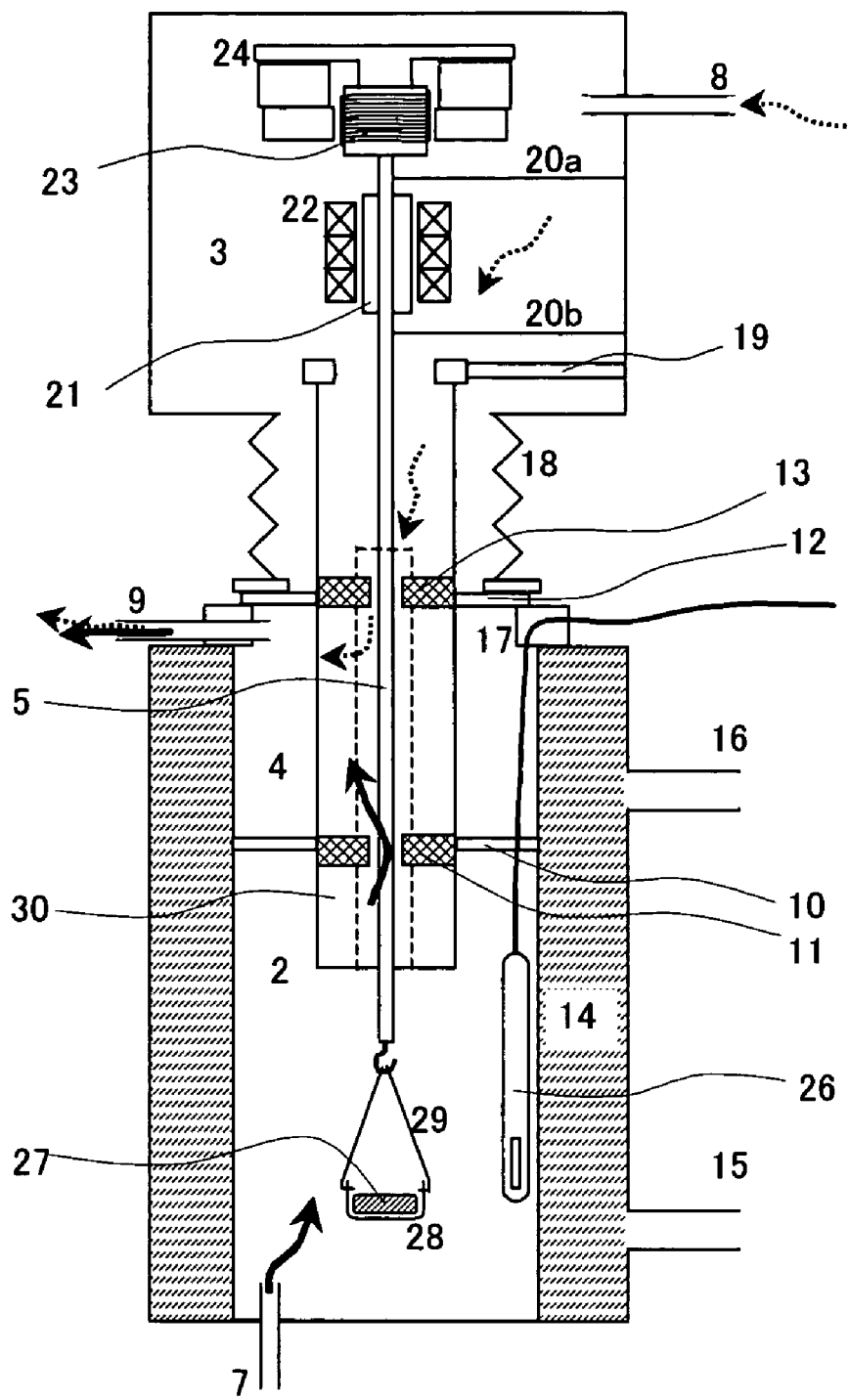
FIG. 3 is a longitudinal sectional view of a vertical-type thermogravimetry device (TG) to which the invention is applied.

FIG. 3 is a longitudinal sectional view of an example in which the invention is applied to a vertical type thermogravimetry device (TG). The vertical type thermogravimetry device (TG) is a device to which the thermomechanical measuring device (TMA) in FIG. 1 is applied. A sample 27 is placed on a sample tray 28, and the sample tray 28 is hung at a lower end of the bar probe 5 serving as a yoke by a sample tray wire 29. A sample tube 30 has a shape obtained by cutting off about lower ⅓ of the sample tube 6 and is opened at a bottom thereof. As a mechanism for performing TG measurement, when feedback control is applied to the electromagnetic load generating coil 23 to hold a displacement signal (TMA signal) at zero, it is possible to measure a change in a load corresponding to a change in a sample weight.

Figure 4:
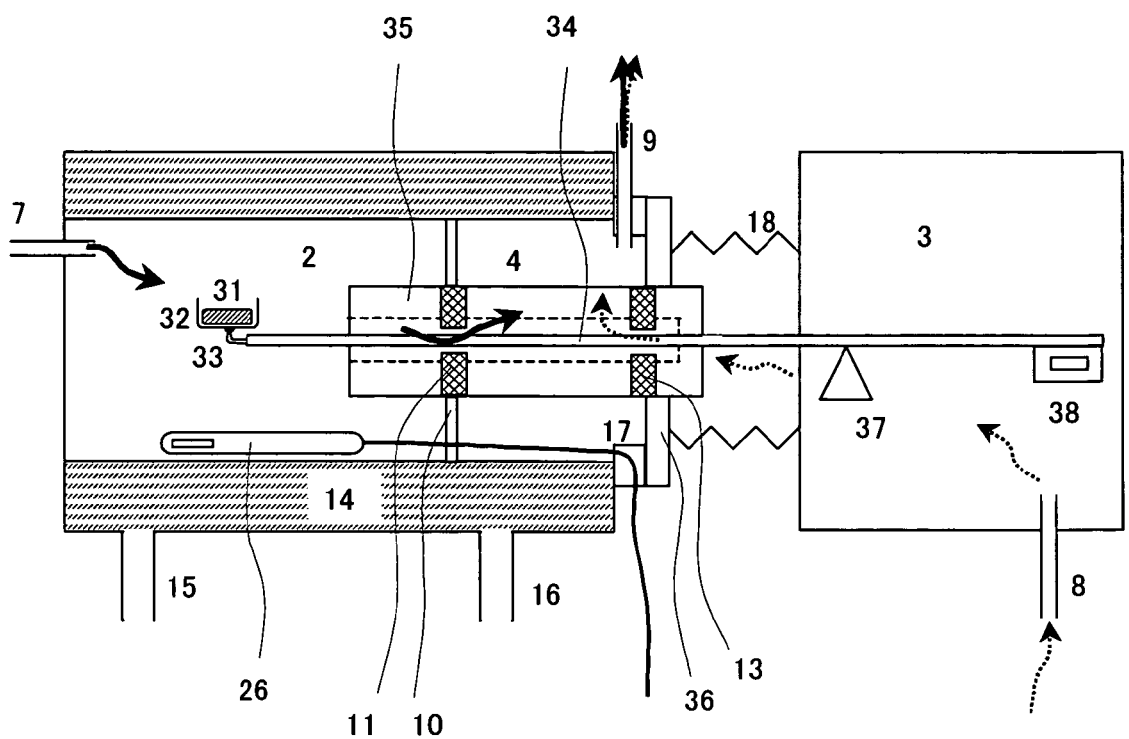
FIG. 4 is a longitudinal sectional view of a horizontal-type thermogravimetry device (TG) to which the invention is applied.
Figure 5:
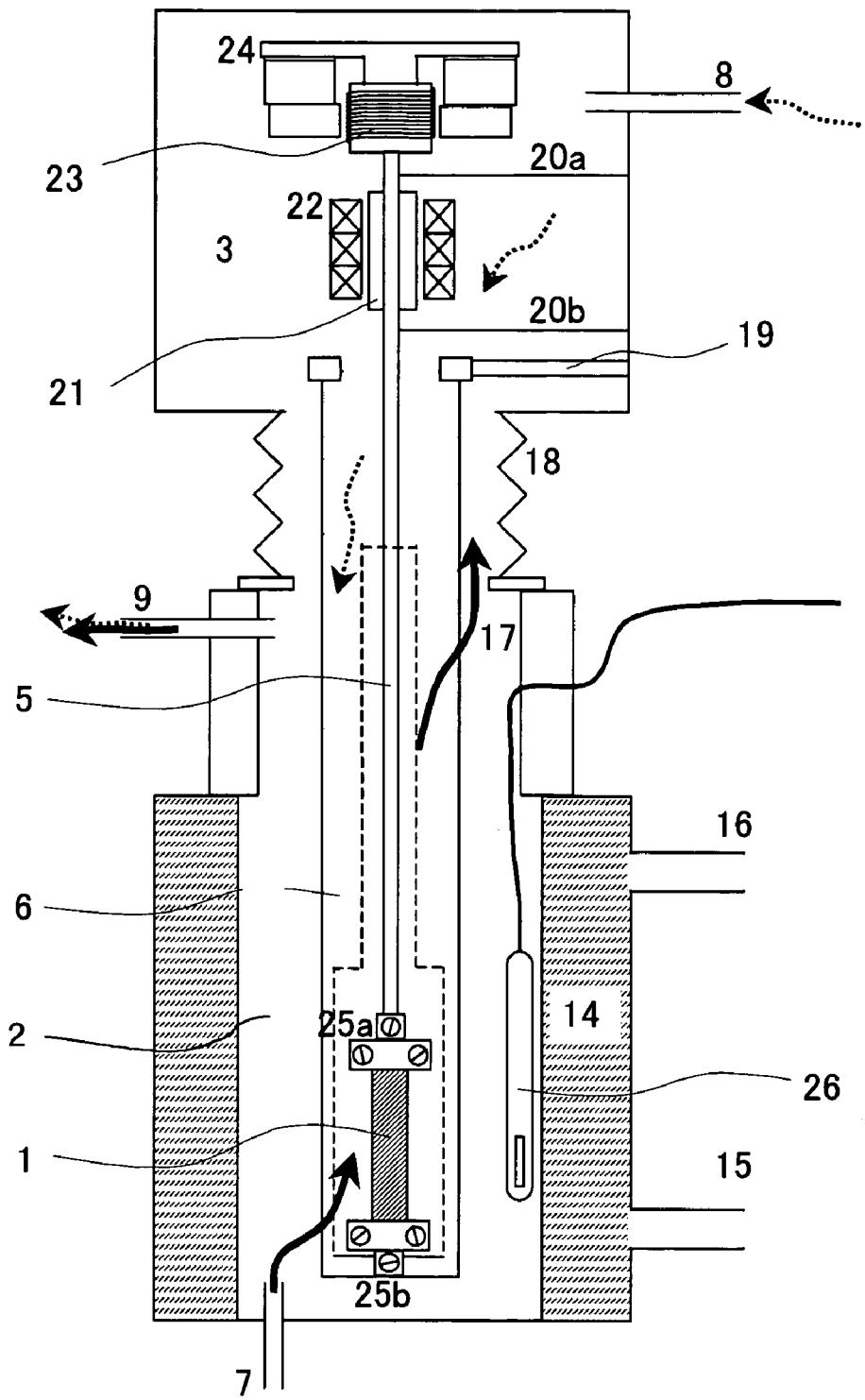
FIG. 5 is a longitudinal sectional view of a thermal analyzer of a conventional example.

FIG. 4 is a longitudinal sectional view of an example in which the invention is applied to a horizontal type thermogravimetry device (TG). A sample 31 is placed on a sample tray 32 held by a thermocouple 33. The thermocouple 33 is inserted through a hole of a balance beam 34, which serves as a yoke, from a tip of the balance beam 34 to measure temperature of the sample 31. In the case of a differential TG device in which a balance beam for reference is also set, the thermocouple 33 is also used for obtaining a differential thermal signal (DTA signal). A gap ring holding cylinder 35 is fixed by a bellows base 36 of a disc ring shape. The gap ring holding cylinder 35 has a cylindrical shape with a vertical slit and holds the gap rings 11 and 13 made of foamed resin on an inner side thereof.

The sample chamber 2 and the gas mixing chamber 4 are partitioned by the disc-like ring 10, which is fixed to the inner wall of the double cylinder hot water furnace 14, and the gap ring 11. The detector chamber 3 and the gas mixing chamber 4 are partitioned by the bellows base 35 and the gap ring 13.

The thermomechanical measuring device and the thermogravimetry device are explained as examples of the invention. The invention effectively acts in these devices but is not limited to these devices.

The invention realizes effects to be described below.

Since the sample chamber and the detector chamber are separated, gasses passing through the sample chamber and the detector chamber are never mixed in the sample chamber and the detector chamber, and it is possible to feed only a target type of gas. Thus, there is an effect that gas purge effect is not damaged.

Since the gas mixing chamber is provided, the two kinds of gasses are mixed and diluted in the inside of the gas mixing chamber. In particular, when a gas containing a high-pressure water vapor gas is fed to the sample chamber side, if a dry gas is fed to the detector side, the gas containing the high-pressure water vapor gas and the dry gas are mixed in the gas mixing chamber. The water vapor gas does not enter the detector chamber, and a water vapor partial pressure in the gas mixing chamber falls due to the mixing of the two kinds of gasses. Consequently, in the detector chamber and the gas mixing chamber, dew points fall and an amount of generation of water drops is reduced when moisture concentration is less likely to occur. Moreover, if a thermal insulation measure is taken, it is possible to substantially eliminate generation of water drops. An error in measurement of a physical amount due to water drops does not occur, and phenomena such as wetting of a sample and unstable relative temperature due to dropping of water drops never occur.

What is claimed is:

1. A thermal analyzer comprising:
   a sample chamber;
   a detector chamber that houses a detector for detecting a physical change due to temperature of a sample disposed in the sample chamber and that is in communication with the sample chamber;
   a bar member that is arranged in the sample chamber at one end thereof and in the detector chamber at the other end thereof and transmits the physical change of the sample to the detector in the detector chamber;
   a first gas introducing section provided in the sample chamber for introducing a first gas into the sample chamber; and
   a second gas introducing section provided in the detector chamber for introducing a second gas into the detector chamber;

a gas mixing chamber that has partition walls on the sample chamber side and the detector chamber side, respectively, and disposed between the sample chamber and the detector chamber;

a gas discharge section provided in a sidewall of the gas mixing chamber; and means defining a through hole through which the bar member is inserted with a gap between the bar member and a wall surface of the through hole.

2. A thermal analyzer for analyzing physical changes of a specimen, comprising:

a sample chamber that stores a sample to be analyzed and in which temperature is variable;

a bar member engageable at one end with the sample and capable of transmitting a physical change of the sample; and a detector chamber that houses the other end of the bar member and a detector for detecting the physical change of the sample, the detector chamber being in communication with the sample chamber;

a gas mixing chamber disposed between the sample and detector chambers with first and second partition walls between the sample chamber and the detector chamber, respectively, and through which the bar member is inserted; wherein the sample chamber has at least two holes for gas flow, the bar member being inserted through one of the two holes that is provided in the first partition wall without coming into contact with a wall surface of the hole, the detector chamber has at least two holes for gas flow, the bar member being inserted through one of the two holes that is provided in the second partition wall without coming into contact with a wall surface of the hole, and the gas mixing chamber has at least three holes for gas flow, two of which holes are provided in the respective first and second partition walls and one of which hole is provided on a side of the gas mixing chamber.

3. A thermal analyzer according to claim 1; wherein of the sample chamber holes, the hole through which the bar member is inserted is an outlet for the gas and the other hole is an inlet for the gas, of the detector chamber holes, the hole through which the bar member is inserted is an outlet for the gas and the other hole is an inlet for the gas, and of the gas mixing chamber holes, the two holes in the partition walls are gas inlets and the hole on the side of the gas mixing chamber is a gas outlet, and the gas inlets of the gas mixing chamber communicate with the outlet for the gas of the sample chamber and the outlet for the gas of the detector chamber, respectively.

4. A thermal analyzer according to claim 3; wherein the sample chamber has a first hole through which the bar member is inserted without coming into contact with a wall surface of the hole and which comprises a sample chamber first outlet for the gas, a second hole provided in the partition wall between the sample chamber and the gas mixing chamber and comprising a sample chamber second outlet for the gas, and a third hole provided on a wall surface different from the partition wall and comprising an inlet for the gas, and a sectional area obtained by cutting the sample chamber second outlet with a partition wall surface around the sample chamber second outlet is larger than a sectional area obtained by cutting a gap formed by the sample chamber first outlet and the bar probe with a partition wall surface around the gap.

5. A thermal analyzer according to claim 3; wherein the detector chamber has a first hole through which the bar member is inserted without coming into contact with a wall surface of the hole and which comprises a detector chamber first outlet for the gas, a second hole provided in the partition wall between the detector chamber and the gas mixing chamber and comprising a detector chamber second outlet for the gas, and a third hole provided on a wall surface different from the partition wall and comprising an inlet for the gas, and a hole area of the detector chamber second outlet is larger than a gap area formed by the detector chamber first outlet and the bar member.

6. A thermal analyzer according to claim 3; wherein the gas fed to the sample chamber is a gas containing a water vapor gas and the gas fed to the detector chamber is a dry gas, and the temperature in the gas mixing chamber is variable to the same temperature as the sample chamber.

* * * * *